United States Patent [19]

Hauschild

[11] Patent Number: 5,424,060
[45] Date of Patent: Jun. 13, 1995

[54] DENTIFRICE COMPOSITION CONTAINING STABILIZED SODIUM PERCARBONATE

[75] Inventor: John P. Hauschild, Bridgewater, N.J.

[73] Assignee: Church & Dwight Co., Inc., Princeton, N.J.

[21] Appl. No.: 254,866

[22] Filed: Jun. 6, 1994

Related U.S. Application Data

[63] Continuation-in-part of Ser. No. 142,856, Oct. 25, 1993, Pat. No. 5,374,368.

[51] Int. Cl.$^6$ .................. A61K 7/16; A61K 7/18; A61K 7/20
[52] U.S. Cl. .................. 424/52; 424/53; 424/56; 424/57; 252/94; 252/174.14; 252/174.21; 252/531; 252/550
[58] Field of Search .................. 252/94, 174.14, 174.21, 252/174.22, 531, 535, 550; 424/52, 53, 56, 57

[56] References Cited

U.S. PATENT DOCUMENTS

| | | | |
|---|---|---|---|
| 4,869,898 | 9/1989 | Gaffar et al. | 424/52 |
| 4,891,211 | 1/1990 | Winston | 424/52 |
| 5,215,740 | 6/1993 | Domke et al. | 424/52 |

Primary Examiner—Paul Lieberman
Assistant Examiner—Lorna M. Douyon
Attorney, Agent, or Firm—Charles B. Barris

[57] ABSTRACT

This invention provides dentifrice compositions which contain sodium bicarbonate abrasive ingredient, and stabilized sodium percarbonate ingredient which releases hydrogen peroxide under dental hygiene utilization conditions. The sodium percarbonate ingredient in a formulated toothpaste composition is stabilized with 0.2–1 part by weight of water per part of sodium percarbonate.

15 Claims, 3 Drawing Sheets

5,424,060

DENTIFRICE COMPOSITION CONTAINING STABILIZED SODIUM PERCARBONATE

CROSS-REFERENCE TO RELATED APPLICATION

This patent application is a continuation-in-part of U.S. patent application Ser. No. 08/142,856, filed Oct. 25, 1993, now U.S. Pat. No. 5,374,368, incorporated herein by reference.

BACKGROUND OF THE INVENTION

Periodontal disease affects a majority of the world's population. The basic cause of the disease is microbial in nature.

It is well-established that hydrogen peroxide and other peroxygen-containing agents are effective in curative and prophylactic treatments with respect to dental plaque, calculus, gingivitis, mouth odor, tooth stains, mucosal infections, and the like.

Most peroxy compounds such as hydrogen peroxide in oral care products tend to be unstable in storage, mainly due to an inherent chemical instability, and also to interaction with other ingredients in the composition. The peroxy compounds decompose within a relatively short period, with a concomitant premature release of active oxygen. Peroxy compounds are difficult to formulate into toothpastes or gels which have an acceptable shelf-life and are capable of liberating active oxygen when applied to an oral cavity.

Many oral care products have been formulated which include a peroxy compound, and more recently oral care products have been developed which include a peroxy compound having improved stability. United States patents which describe peroxy-containing toothpastes, mouthwashes, tablets, chewing gums, and other forms of oral care products include U.S. Pat. Nos. 2,275,979; 3,577,521; 3,657,413; 3,885,028; 3,886,265; 4,226,851; 4,302,441; 4,405,599; 4,426,108; 4,431,631; 4,521,403; 4,522,805; 4,528,180; 4,567,036; 4,592,487; 4,592,488; 4,592,489; 4,687,663; 4,812,308; 4,837,008; 4,839,157; 4,849,213; 4,867,988; 4,891,211; 4,897,258; 4,925,655; 4,971,782; 4,980,152; 4,988,450; 5,000,941; 5,041,280; 5,085,853; 5,256,402; and the like; incorporated by reference.

Both organic and inorganic peroxy compounds have been proposed for use in oral care products, and typically the peroxy compounds exhibit one or more disadvantages which limit their effectiveness in oral hygiene applications.

Sodium perborate and potassium chlorate do not release significant levels of hydrogen peroxide in water. Sodium perborate also is of questionable safety because it contains boron which can undergo systemic absorption.

Sodium percarbonate has a high active oxygen content (15.28% theoretical) and high water solubility. It is produced from low cost starting materials, and it is an environmentally safe chemical. Sodium percarbonate is potentially a superior reagent as a hydrogen peroxide-releasing ingredient in oral care products, except that it is less stable than sodium perborate.

Stabilizers such as magnesium sulfate are suitable for stabilizing sodium perborate, but provide only limited protection with sodium percarbonate. Various methods for stabilization of sodium percarbonate have been proposed.

U.S. Pat. No. 2,380,620 discloses that sodium silicate, magnesium sulphate or gum arabic are unsatisfactory stabilizers when incorporated in sodium percarbonate, but diphenylguanidine lessens the decomposition in the presence of the conventional stabilizers.

U.S. Pat. No. 3,951,838 discloses that prior attempts at chemical stabilization of sodium percarbonate, primarily by magnesium silicate, are generally ineffective in promoting long term stability, particularly in a humid atmosphere. The patent proposes coating of the particles with an aqueous silica sol and drying to accomplish stabilization.

U.S. Pat. No. 4,075,116 describes cocrystallizing of sodium percarbonate with other salts known to form perhydrates such as sodium sulfate, sodium pyrophosphate, sodium glucoheptonate, sodium metaborate, and the like.

U.S. Pat. No. 4,171,28.0 discloses that a non-caking bleach composition may be formed containing up to 6% active oxygen by spraying only sufficient hydrogen peroxide onto sodium carbonate particles to convert a part of the sodium carbonate to sodium percarbonate. U.S. Pat. No. 4,260,408 teaches the addition of sodium phosphate to the composition as a stabilizer. Both patents demonstrate that an assay of less than 6% active oxygen (less than 40% sodium percarbonate) is necessary to obtain satisfactory stability.

There is continuing research and development effort to produce sodium percarbonate in a form which exhibits long term stability under storage conditions, and when incorporated as a peroxygen ingredient in commercial products.

Accordingly, it is an object of this invention to provide sodium percarbonate in a form which is stable under ambient temperature and moisture conditions.

It is a further object of this invention to provide a dentifrice composition which contains stabilized sodium percarbonate, and which releases active oxygen under oral hygiene utilization conditions.

Other objects and advantages of the present invention shall become apparent from the accompanying description and examples.

DESCRIPTION OF THE INVENTION

Figure 1:
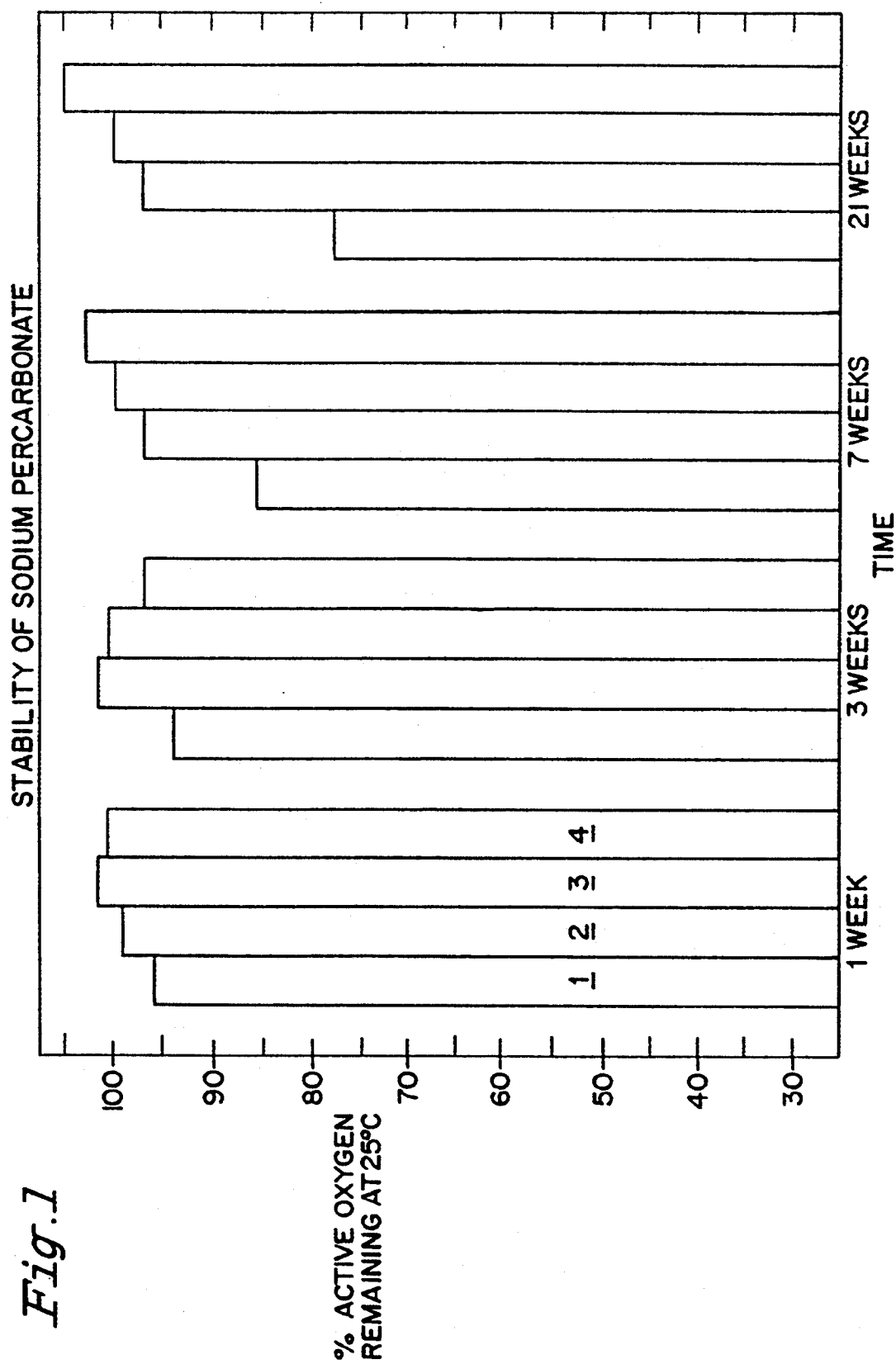
FIGS. 1–3 are bar graphs showing the comparative stability of sodium percarbonate at different formulations.

One or more objects of the present invention are accomplished by the provision of a dentifrice composition comprising (1) between about 20–50 weight percent of polyalkylene glycol; (2) between about 1–15 weight percent of sodium percarbonate; (3) between about 30–60 weight percent of sodium bicarbonate; (4) between about 0.1–5 weight percent of colloidal silica; (5) between about 0.05–0.5 weight percent of fluoridating ingredient; (6) between about 0.2–2 weight percent of alkali metal $C_{10}$–$C_{18}$ alkyl sulfate anionic surfactant; (7) between about 0.2–2 weight percent of alkali metal $C_{10}$–$C_{18}$ acylsarcosinate anionic surfactant; (8) between about 1–8 weight percent of nonionic surfactant; and (9) between about 0.2–1 part by weight of water per part of sodium percarbonate.

An important advantage of a present invention dentifrice composition is the long term stability of the sodium percarbonate ingredient, which releases hydrogen peroxide under dentifrice utilization conditions. The dentifrice composition in the form of a toothpaste formation provides active oxygen in the oral cavity during dental brushing. The sodium percarbonate content of an invention toothpaste formulation does not degrade and generate gas during storage in a capped toothpaste tube over a period of six months under ambient conditions.

The polyalkylene glycol ingredient of an invention dentifrice composition preferably is selected from oxyalkylated diols which have a molecular weight in the range between about 400–12,000. Polyethylene glycols are commercially available under tradenames such as Carbowax 200, 300, 400, 600, 900, 1000, 20000, 4000, 6000 and 8000 (Union Carbide), in which the number values are approximations of average molecular weight. Polyethylene-propylene glycols are commercially available under tradenames such as Pluracare/Pluronic L-31 and L-35 (BASF).

The polyalkylene glycol ingredient serves as a hydrophilic vehicle for the other dentifrice ingredients. It enhances the compatibility of the ingredients when they are incorporated as constituents in a dentifrice composition.

The sodium percarbonate ingredient of an invention dentifrice composition is employed in the form of a crystalline powder, which typically has an average particle size between about 1–100 microns, and preferably the particle size is in the range of 5–40 microns. Methods of manufacturing sodium percarbonate are described in technical publications such as U.S. Pat. No. 4,966,762 and references cited therein.

An essential aspect of a present invention dentifrice composition is the inclusion of a controlled quantity of water content. As demonstrated in Example I, the sodium percarbonate ingredient in a dentifrice formulation is stabilized against degradation by the inclusion of between about 0.2–1 part by weight of water per part of sodium percarbonate.

The sodium bicarbonate ingredient of an invention dentifrice composition functions as a soft abrasive, and additionally it imparts a clean and fresh feel in the oral cavity when an invention toothpaste formulation is utilized. The sodium bicarbonate preferably has an average particle size between about 5–200 microns.

The colloidal silica ingredient of an invention dentifrice composition can be selected from amorphous silica compounds which function as a thickening agent relative to the polyalkylene glycol ingredient. Commercial colloidal silica compounds are available under tradenames such as Sylodent 15 and Sylodent 2 (W. R. Grace), Aerosil 200 (Degussa) and Cabosil fumed silica (Cabot). The colloidal silica ingredient is compatible with the polyalkylene glycol ingredient.

Aerosil 200 is a preferred type of hydrophilic fumed silica having a surface area of about 200 $M^2/g$, and an average particle size between about 10–12 nanometers. Aerosil R972 is a hydrophobic fumed silica having a surface area of about 100 $M^2/g$, and an average particle size of about 15 nanometers.

The alkali metal $C_{10}$–$C_{18}$ alkyl sulfate anionic surfactant ingredient of an invention dentifrice composition is illustrated by surface-active compounds such as sodium and potassium salts of sulfate esters of n-decanol, n-tridecanol, lauryl alcohol, myristyl alcohol, cetyl alcohol, and stearyl alcohol.

The alkali metal $C_{10}$–$C_{18}$ acylsarcosinate anionic surfactant ingredient is illustrated by surface-active compounds such as sodium and potassium salts of sarcosine aminoacid, which are N-substituted with acyl groups derived from fatty acids which include capric acid, lauric acid, myristic acid, palmitic acid, stearic acid, oleic acid, and the like.

The nonionic surfactant ingredient of an invention dentifrice composition is selected from surface-active organic polymers which include polyethylene-polypropylene block polymers (Pluronics); $C_6$–$C_{18}$ alcohols with 1–15 moles of ethylene oxide per mole of alcohol; $C_6$–$C_{18}$ alcohols with 1–10 moles of propylene oxide per mole of alcohol; $C_6$–$C_{18}$ alcohols with 1–15 moles of ethylene oxide and 1–10 moles of propylene oxide per mole of alcohol; $C_6$–$C_{18}$ alkylphenols with 1–15 moles of ethylene oxide and/or propylene oxide; polyoxyethylene monoester of sorbitol with a $C_{10}$–$C_{18}$ fatty acid, such as Polysorbate 20 [polyoxyethylene (20)sorbitan monolaurate]; and the like.

The nonionic surfactant provides solubilizing, dispersing and emulsifying activities relative to the other dentifrice composition ingredients. The two anionic surfactant ingredients contribute additional surface-active functions, and the combination of three surfactant ingredients also provides an effective foaming action during dental hygiene brushing with an invention toothpaste formulation.

The fluoridating ingredient of an invention dentifrice is selected from fluoride-providing salts which have anti-caries efficacy. Suitable salts include sodium fluoride; potassium fluoride; cuprous fluoride; stannous fluoride; stannous chlorofluoride; sodium fluorosilicate; ammonium fluorosilicate; sodium monofluorophosphate; and the like.

The anticalculus efficacy of an invention dentifrice composition can be increased by the addition of between about 0.5–10 weight percent of an alkali metal pyrophosphate ingredient. Suitable alkali metal pyrophosphates include dialkali metal and tetraalkali metal pyrophosphate and mixtures thereof in a hydrated or unhydrated form. Illustrative of pyrophosphate salts are $Na_2H_2P_2O_7$, $Na_4P_2O_7$ and $K_4P_2O_7$.

A toothpaste formulation can be prepared conveniently by blending each of the ingredients into the polyalkylene glycol ingredient, which normally is a viscous liquid at room temperature. Conventional adjuvants can be included.

Suitable adjuvants include whitening agents such as titanium dioxide; preservatives; silicones; chlorophyll compounds; antibacterial agents such as cetyl pyridinium chloride; flavorants such as oils of spearmint and peppermint; sweetening agents such as sucrose, saccharin, aspartame and sodium cyclamate; colorants such as FDC Red 40, FDC Green 3, DC Red 19 and D&C Green 5; humectants such as glycerin; gelling agents such as sodium carboxymethylcellulose; abrasives such as alpha-alumina, particulate polyvinyl chloride, and calcium phosphate; and the like.

A flavorant is employed in a quantity between about 0.2–2 weight percent. A sweetener ingredient is employed in a quantity between about 0.1–5 weight percent, and a colorant additive quantity is between about 0.005–0.3 weight percent.

By the practice of the present invention, an oral care product can be prepared which has superior properties for retarding plaque and calculus formulation, and controlling bad breath and gingivitis. Important advantages derive from the presence of stabilized sodium percarbonate as a component of an oral care product, when the oral care product is applied to an oral cavity following a prescribed hygiene regimen.

As an alternative ingredient to sodium percarbonate, the present invention also contemplates the use of other stabilized inorganic peroxyhydrate compounds which yield hydrogen peroxide when dissolved in an aqueous medium, such as sodium pyrophosphate peroxyhydrate.

The following examples are further illustrative of the present invention. The components and specific ingredients are presented as being typical, and various modifications can be derived in view of the foregoing disclosure within the scope of the invention.

Figure 2:
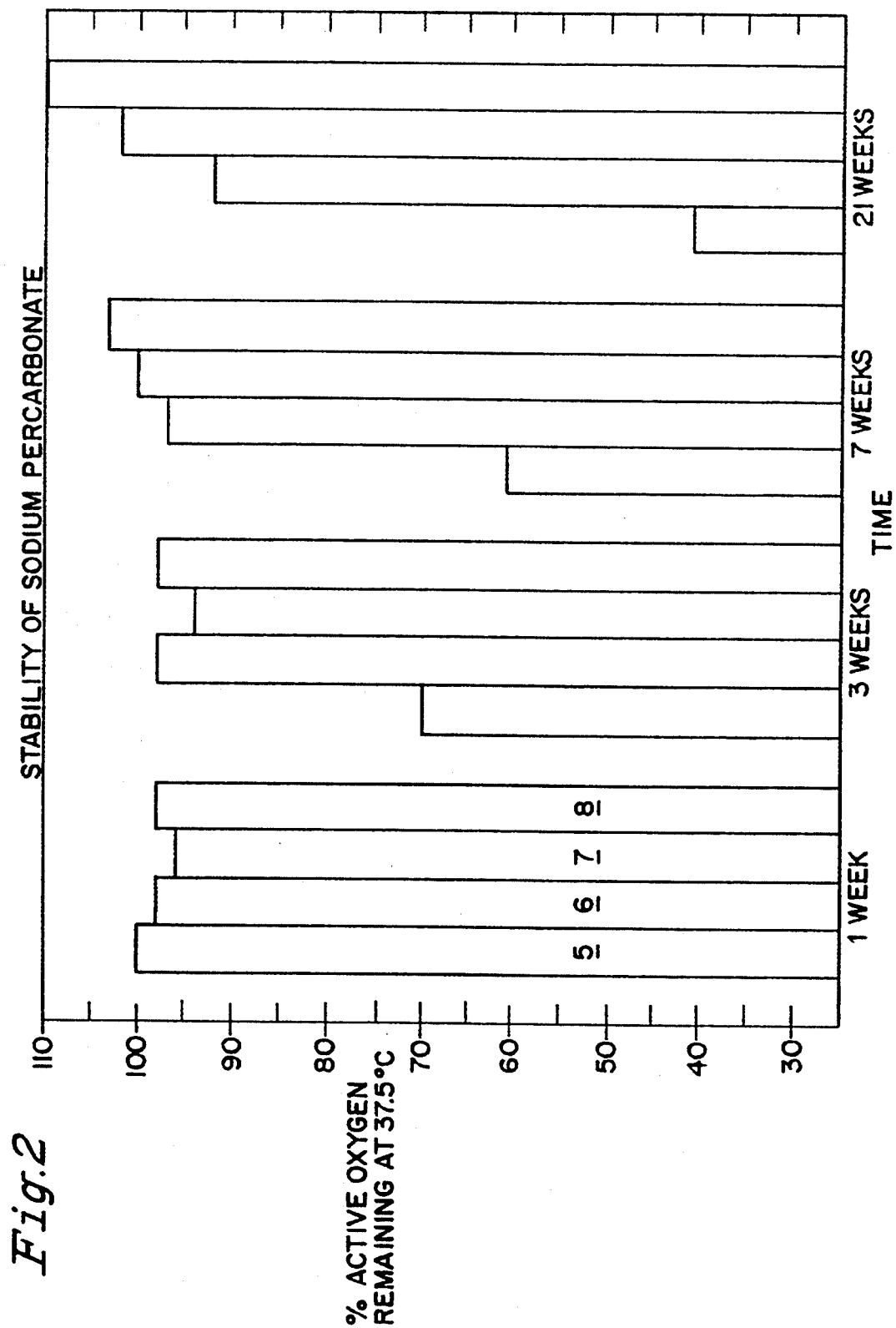
Figure 3:
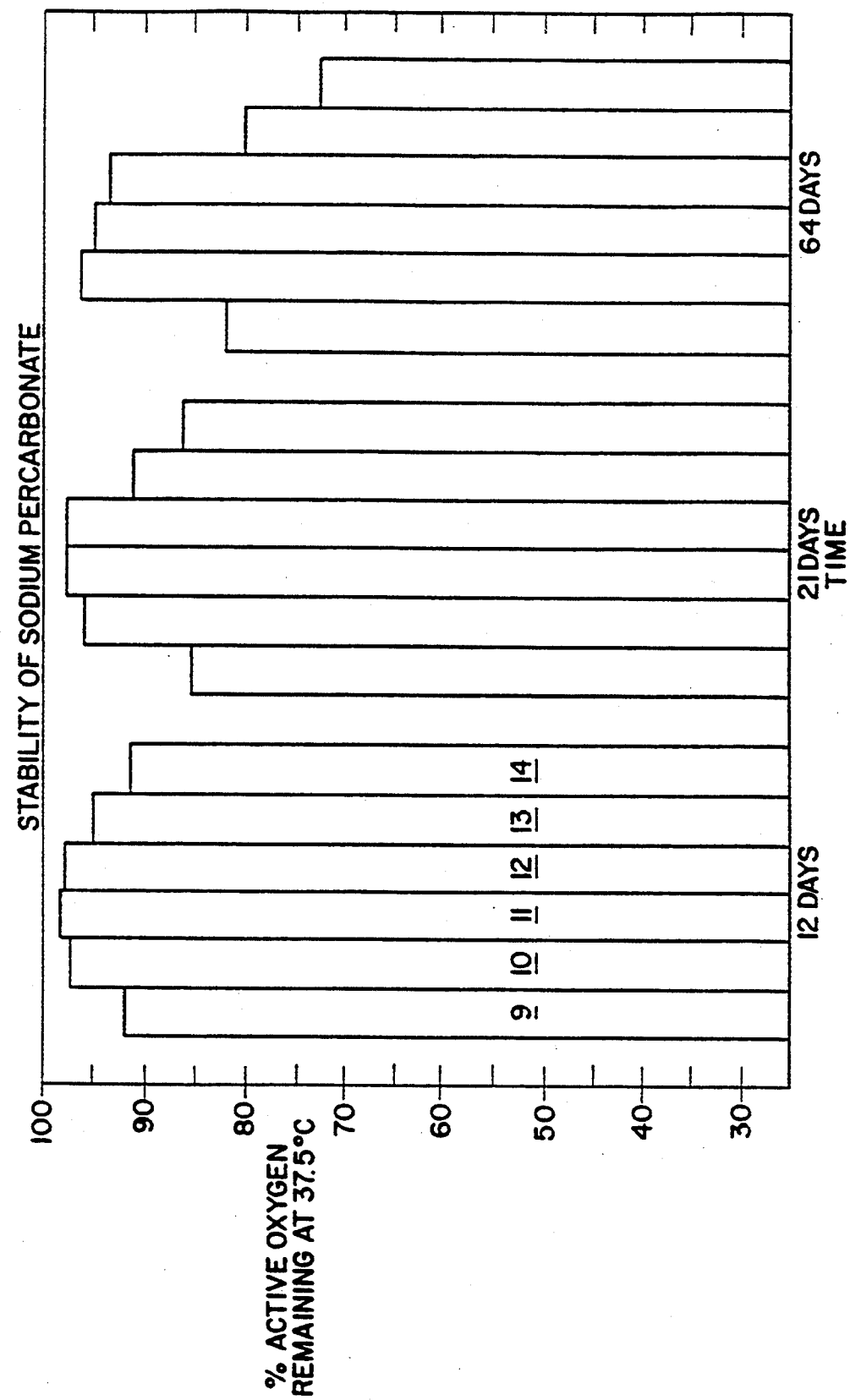

FIGS. 1-3 are bar graphs which are a representation of the comparative stability data corresponding to the 14 formulations as prepared and tested in Example I.

For test purposes in Example I, the level of active oxygen content retained in each formulation under simulated storage conditions is determined as follows:

A 1-2 gram sample of a formulation is weighted accurately, and transferred into a 250 ml Erlenmeyer flask. A 75-100 ml aliquot of 3M sulfuric acid is added dropwise while the flask contents are swirled gently. The acidified aqueous medium then is titrated with 0.1N KMnO$_4$ solution until a permanent pink color is evident.

$$\text{active oxygen} = \frac{V \times N \times 0.8}{\text{Sample weight (grams)}}$$

where V is ml of KMnO$_4$ solution consumed; and N is normality of KMnO$_4$ solution.

EXAMPLE I

This Example illustrates the stability of hydrogen peroxide-releasing formulations in accordance with the present invention.

A series of gel formulations are prepared by blending the ingredients listed in the Table.

The effect of water content on the stability of sodium percarbonate is tested for the 14 formulations in the Table. FIGS. 1-3 are bar graphs which summarize the comparative stability data at temperatures of 25° C. and 37.5° C. over extended periods of time.

The comparative data demonstrate that the highest sodium percarbonate stability is exhibited by gel formulations which have a water content between about 0.2-1 part by weight per part of sodium percarbonate.

TABLE

| Ingredient Parts By Weight | Formulation Numbers | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Polyethylene glycol (M.W. 400) | 34 | 33 | 31 | 29 | 34 | 33 | 31 | 29 | 34 | 32 | 30 | 28 | 26 | 26 |
| Deionized water | 0 | 1 | 3 | 5 | 0 | 1 | 3 | 5 | 0 | 2 | 4 | 6 | 8 | 10 |
| Sodium percarbonate | 6 | 6 | 6 | 6 | 6 | 6 | 6 | 6 | 6 | 6 | 6 | 6 | 6 | 6 |
| Aerosil 200 (Degussa) | 1 | 1 | 1 | 1 | 1 | 1 | 1 | 1 | 1 | 1 | 1 | 1 | 1 | 1 |
| Tetrasodium pyrophosphate | 0.5 | 0.5 | 0.5 | 0.5 | 0.5 | 0.5 | 0.5 | 0.5 | 0.5 | 0.5 | 0.5 | 0.5 | 0.5 | 0.5 |

EXAMPLE II

This Example illustrates the preparation of a stable dentifrice composition in accordance with the present invention.

A pre-blend is prepared with the following ingredients:

| | Parts By Weight |
|---|---|
| Polyethylene glycol (M.W. 400) | 34.45 |
| Polyethylene glycol (M.W. 8000) | 0.9 |
| Sodium percarbonate | 6.0 |
| Aerosil 200 (Degussa) | 1.0 |
| Tetrasodium pyrophosphate | 2.0 |
| Water | 2.0 |

The pre-blend is admixed with additional ingredients to form a composition with a toothpaste consistency:

| | Weight Percent |
|---|---|
| Polyethylene glycol (M.W. 400) | 34.45 |
| Polyethylene glycol (M.W. 8000) | 0.9 |
| Sodium percarbonate | 6.0 |
| Aerosil 200 (Degussa) | 1.0 |
| Tetrasodium pyrophosphate | 2.0 |
| Water | 2.0 |
| Sodium bicarbonate | 51.0 |
| Flavor | 0.75 |
| Saccharin | 0.9 |
| Sodium lauryl sulfate | 1.0 |

The invention toothpaste is more stable than a control toothpaste which has a zero weight percent water content, when tested at 37.5° C. for 21 days. The invention toothpaste has an active oxygen loss of about 4%, and the control toothpaste has an active oxygen loss in the range of about 10-14 percent.

It is advantageous to minimize the presence of any polyvalent metal ions such as copper, iron, manganese, nickel, and the like, in the formulations, since this type of impurity tends to catalyze the decomposition of peroxygen compounds.

EXAMPLE III

This Example illustrates the preparation of a stable toothpaste formulation in accordance with the present invention.

A formulation with a toothpaste consistency is prepared by blending the following ingredients:

| | Parts By Weight |
|---|---|
| PEG-8[1] | 34.50 |
| Sodium fluoride | 0.25 |
| Sodium saccharin | 1.10 |
| Sodium lauryl sulfate | 0.50 |
| Sodium lauroyl sarcosinate | 0.50 |
| Flavorant 279194[2] | 1.20 |
| Sodium bicarbonate[3] | 50.32 |
| Pluronic F-127 (BASF)[4] | 5.00 |
| Aerosil 200 (Degussa) | 2.50 |
| Sodium percarbonate[5] | 3.00 |
| Water | 1.20 |

[1] Polyethylene glycol (M.W. 400).
[2] Haarmann & Reimer.
[3] Grade 3; Church & Dwight Co.
[4] Polyoxyethylene-polyoxypropylene block polymer.
[5] 5-40 Micron particle size range.

The final homogeneous formulation is deaerated and filled into standard capped toothpaste tubes. After storage at 25° C. for 21 weeks, the capped tubes do not show any evidence of tube distortion from gas generation within the dentifrice contents.

What is claimed is:

1. A dentifrice composition comprising (1) between about 20–50 weight percent of polyalkylene glycol; (2) between about 1–15 weight percent of sodium percarbonate; (3) between about 30–60 weight percent of sodium bicarbonate; (4) between about 0.1–5 weight percent of colloidal silica; (5) between about 0.05–0.5 weight percent of fluoridating ingredient; (6) between about 0.2–2 weight percent of alkali metal $C_{10}$–$C_{18}$ alkyl sulfate anionic surfactant; (7) between about 0.2–2 weight percent of alkali metal $C_{10}$–$C_{18}$ acylsarcosinate anionic surfactant; (8) between about 1–8 weight percent of nonionic surfactant; and (9) between about 0.2–1 part by weight of water per part of sodium percarbonate.

2. A dentifrice composition in accordance with claim 1 wherein the polyalkylene glycol ingredient is polyethylene glycol having an average molecular weight between about 400–12,000.

3. A dentifrice composition in accordance with claim 1 wherein the sodium percarbonate ingredient has an average particle size between about 1–100 microns.

4. A dentifrice composition in accordance with claim 1 wherein the sodium bicarbonate ingredient has an average particle size between about 5–200 microns.

5. A dentifrice composition in accordance with claim 1 wherein the colloidal silica ingredient is fumed silica.

6. A dentifrice composition in accordance with claim 1 wherein the fluoridating ingredient is sodium fluoride.

7. A dentifrice composition in accordance with claim 1 wherein the sulfate anionic surfactant is sodium lauryl sulfate.

8. A dentifrice composition in accordance with claim 1 wherein the acylsarcosinate anionic surfactant is sodium lauroyl sarcosinate.

9. A dentifrice composition in accordance with claim 1 wherein the nonionic surfactant is a polyoxyethylene-polyoxypropylene block polymer.

10. A dentifrice composition in accordance with claim 1 which contains between about 0.5–10 weight percent of alkali metal pyrophosphate ingredient.

11. A dentifrice composition in accordance with claim 1 which contains between about 0.2–2 weight percent of flavorant ingredient.

12. A dentifrice composition in accordance with claim 1 which contains between about 0.1–5 weight percent of sweetener ingredient.

13. A dentifrice composition in accordance with claim 1 which contains between about 0.005–0.3 weight percent of colorant ingredient.

14. A method of retarding dental plaque and calculus formation in an oral cavity which comprises applying a claim 1 dentifrice composition to the oral cavity in accordance with a prescribed hygiene regimen.

15. A dentifrice composition in accordance with claim 1 wherein the surfactant ingredients comprise sodium lauryl sulfate, sodium lauroyl sarcosinate and polyoxyethylene-polypropylene block polymer.

* * * * *